(12) United States Patent
Yeung et al.

(10) Patent No.: US 8,088,150 B2
(45) Date of Patent: Jan. 3, 2012

(54) DEVICE FOR DISC SHUNT IMPLANTATION AND PERI-SHUNT INJECTION

(75) Inventors: Jeffrey E. Yeung, San Jose, CA (US); Teresa T. Yeung, San Jose, CA (US)

(73) Assignee: Aleeva Medical Inc., San Jose, CA (US)

( * ) Notice: Subject to any disclaimer, the term of this patent is extended or adjusted under 35 U.S.C. 154(b) by 355 days.

(21) Appl. No.: 12/322,570

(22) Filed: Feb. 4, 2009

(65) Prior Publication Data

US 2009/0198248 A1   Aug. 6, 2009

Related U.S. Application Data

(60) Provisional application No. 61/063,473, filed on Feb. 4, 2008, provisional application No. 61/065,037, filed on Feb. 8, 2008, provisional application No. 61/072,019, filed on Mar. 26, 2008, provisional application No. 61/125,016, filed on Apr. 21, 2008.

(51) Int. Cl.
*A61B 17/88* (2006.01)
(52) U.S. Cl. .......................................... 606/279
(58) Field of Classification Search ............... 606/86 A, 606/248, 279, 297
See application file for complete search history.

(56) References Cited

U.S. PATENT DOCUMENTS

| | | | |
|---|---|---|---|
| 3,094,122 A * | 6/1963 | Gauthier et al. | 604/164.01 |
| 5,895,395 A * | 4/1999 | Yeung | 606/144 |
| 6,562,033 B2 * | 5/2003 | Shah et al. | 606/41 |
| 7,553,307 B2 * | 6/2009 | Bleich et al. | 606/1 |
| 7,785,314 B2 * | 8/2010 | Miller et al. | 604/508 |
| 7,879,097 B2 * | 2/2011 | Lambrecht et al. | 623/17.11 |
| 7,909,851 B2 * | 3/2011 | Stone et al. | 606/232 |
| 2003/0028147 A1 * | 2/2003 | Aves et al. | 604/164.06 |
| 2005/0240201 A1 * | 10/2005 | Yeung | 606/108 |
| 2005/0246023 A1 * | 11/2005 | Yeung | 623/17.11 |
| 2006/0089609 A1 * | 4/2006 | Bleich et al. | 604/272 |
| 2006/0247600 A1 * | 11/2006 | Yeung et al. | 604/500 |
| 2007/0142791 A1 * | 6/2007 | Yeung et al. | 604/264 |
| 2007/0169911 A1 * | 7/2007 | Yeung et al. | 164/10 |
| 2007/0265561 A1 * | 11/2007 | Yeung | 604/27 |
| 2008/0103504 A1 * | 5/2008 | Schmitz et al. | 606/79 |
| 2008/0200972 A1 * | 8/2008 | Rittman et al. | 607/117 |
| 2008/0312636 A1 * | 12/2008 | Miller et al. | 604/508 |
| 2009/0254061 A1 * | 10/2009 | Baron | 604/506 |
| 2010/0030105 A1 * | 2/2010 | Noishiki et al. | 600/567 |
| 2010/0030241 A1 * | 2/2010 | Yeung et al. | 606/146 |

* cited by examiner

*Primary Examiner* — Nicholas Lucchesi
*Assistant Examiner* — Diva Ranade
(74) *Attorney, Agent, or Firm* — Carol Titus; GSS Law Group

(57) ABSTRACT

A Quincke tipped introducer needle contains two shafts with lumens, one recessed, both connected by a slit for housing a U- or V-shaped disc shunt. The recessed shaft minimizes the penetration size of the introducer needle for insertion into a narrow and nerve laden space adjacent to a degenerated intervertebral disc. The longitudinal slit connecting the two lumens allows passage of the distal portion of the U-shaped disc shunt through the introducer needle, to be delivered into the intervertebral disc.

Pain emitting from the avascular disc is extremely difficult to treat due to lack of penetration or permeability of drug. The lumens of the introducer needle are also used to retain a peri-shunt injectable into the disc shunt for delivery into the painful disc. The peri-shunt injectable can be an analgesic, narcotic, anti-inflammatory drug, antibiotic, anticonvulsant, antidepressant, buffer agent or alkaline agent to alleviate pain. The peri-shunt injectable can also be a nerve toxin retained within the lumens to be loaded within the shunt for terminating transmission of pain signal emitting from the disc.

43 Claims, 12 Drawing Sheets

DEVICE FOR DISC SHUNT IMPLANTATION AND PERI-SHUNT INJECTION

CROSS-REFERENCE TO OTHER APPLICATIONS

This application claims priority of the U.S. Provisional Applications 61/063,473, filed on Feb. 4, 2008; 61/065,037, filed on Feb. 8, 2008; 61/072,019, filed on Mar. 26, 2008; and 61/125,016 filed on Apr. 21, 2008.

FIELD OF INVENTION

This invention relates to a delivery device and method to maximize safety for implantation of a disc shunt and to infuse drugs, nutrients, buffer agents or growth factors through the disc shunt to treat back pain.

BACKGROUND

Low back pain is a leading cause of disability and lost productivity. Up to 90% of adults experience back pain at some time during their lives. Among frequency of physician visits, back pain is second only to upper respiratory infections. In the United States, this malady disables 5.2 million people, and the economic impact has been reported to be as high as $100 billion each year. Though the sources of low back pain are varied, in most cases the intervertebral disc is thought to play a central role.

The intervertebral disc absorbs most of the compressive load of the spine, but the facet joints of the vertebral bodies share approximately 16%. The disc consists of three distinct parts: the nucleus pulposus, the annular layers and the cartilaginous endplates. The disc maintains its structural properties largely through its ability to attract and retain water. A normal disc contains 80% water in the nucleus pulposus. The nucleus pulposus within a normal disc is rich in water absorbing sulfated glycosaminoglycans (chondroitin and keratan sulfate), creating swelling pressure to provide tensile stress within the collagen fibers of the annulus. The swelling pressure produced by high water content is crucial to supporting the annular layers and sustaining compressive loads.

In adults, the intervertebral disc is avascular. Survival of the disc cells depends on diffusion of nutrients from external blood vessels and capillaries through the cartilage of the endplates. Diffusion of nutrients also permeates from peripheral blood vessels adjacent to the outer annulus, but these nutrients can only permeate up to 1 cm into the annular layers of the disc. An adult disc can be as large as 5 cm in diameter; hence diffusion through the cranial and caudal endplates is crucial for maintaining the health of the nucleus pulposus and inner annular layers of the disc.

Calcium pyrophosphate and hydroxyapatite are commonly found in the endplate and nucleus pulposus. Beginning as young as 18 years of age, calcified layers begin to accumulate in the cartilaginous endplate. The blood vessels and capillaries at the bone-cartilage interface are gradually occluded by the build-up of the calcified layers which form into bone. Bone formation at the endplate increases with age.

When the endplate is obliterated by bone, diffusion of nutrients through the calcified endplate is greatly limited. In addition to hindering the diffusion of nutrients, calcified endplates further limit the permeation of oxygen into the disc.

The supply of sulfate into the nucleus pulposus for biosynthesizing sulfated glycosaminoglycans is also restricted by the calcified endplates. As a result, the sulfated glycosaminoglycan concentration decreases, leading to lower water content and swelling pressure within the nucleus pulposus. During normal daily compressive loading on the spine, the reduced pressure within the nucleus pulposus can no longer sustain most of the compressive load. The load is then transferred from the flattened disc to strain the facet joints, causing wear and pain.

The shear stresses on the disc are the highest at the posterolateral sides, adjacent to the neuroforamen. The nerve is confined within the neuroforamen between the disc and the facet joint. Hence, the nerve at the neuroforamen is vulnerable to impingement by the bulging disc or bone spurs.

When oxygen concentration in the disc is low, production of lactic acid dramatically increases. The pH within the disc falls as lactic acid concentration increases. Lactic acid diffuses through micro-tears of the annulus, irritating the richly innervated posterior longitudinal ligament, facet joint and/or nerve root. Studies indicate that lumbar pain correlates well with high lactate levels and low pH. The mean pH of symptomatic discs was significantly lower than the mean pH of normal discs. Acid concentration can be three times higher in symptomatic discs than normal discs. In symptomatic discs with pH 6.65, the acid concentration within the disc is 5.6 times the plasma level. In some preoperative symptomatic discs, nerve roots were found to be surrounded by dense fibrous scars with remarkably low pH 5.7-6.30. The acid concentration within these discs was 50 times the plasma level.

Approximately 85% of patients with low back pain cannot be given a precise pathoanatomical diagnosis. This type of pain is generally classified under "non-specific pain." Back pain and sciatica can be recapitulated by maneuvers that do not affect the nerve root, such as intradiscal saline injection, discography, and compression of the posterior longitudinal ligaments. It is possible that some of the non-specific pain is caused by lactic acid irritation secreted from the disc. Injection into the disc can flush out the lactic acid. Maneuvering and compression can also drive out the irritating acid and produce non-specific pain. Currently, no intervention other than discectomy can halt the production of lactic acid.

In the presence of oxygen, metabolism of each glucose molecule produces 36 adenosine triphosphates, ATP, through glycolysis, citric acid cycle and the electron transport chain. ATP is a high-energy compound essential for driving biosynthesis of water-retaining proteoglycans. Under anaerobic conditions, the metabolism of each glucose molecule produces only 2 ATP and two lactic acids. Hence, production of high-energy compound ATP is low under anaerobic conditions, while production of lactic acid is high within the degenerated disc.

The nucleus pulposus is thought to function as "the air in a tire" to pressurize the disc. To support the load, the pressure effectively distributes the forces evenly along the circumference of the inner annulus and keeps the lamellae bulging outward. The process of disc degeneration begins with calcification of the endplates, which hinders diffusion of sulfate and oxygen into the nucleus pulposus. As a result, production of the water absorbing sulfated glycosaminoglycans is significantly reduced, and the water content within the nucleus decreases. The inner annular lamellae begin to sag inward, and the tension on collagen fibers within the annulus is lost. The degenerated disc exhibits unstable movement, similar to a flat tire. Approximately 20-30% of low back pain patients have been diagnosed as having spinal segmental instability. The pain may originate from stress and increased load on the facet joints and/or surrounding ligaments. In addition, pH within the disc becomes acidic from the anaerobic production of lactic acid, which irritates adjacent nerves and tissues.

Inflammation or infection within the intervertebral disc is extremely difficult to treat due to inaccessibility of drugs. Persistent pain emitting from the avascular disc is common. Intensity of the pain often is excruciating and disabling with limited options.

The method of endplate puncturing for drawing nutrients from the vertebral body to regenerate the degenerated disc is described in PCT/US2002/04301 (US national application Ser. No. 10/470,181) filed on Feb. 13, 2002 by J. Yeung and T. Yeung.

Shunts or conduits for re-establishing the exchange of nutrients and waste between the degenerative disc and body circulation is described in PCT/US2004/014368 (US national application Ser. No. 10/555,895) filed on May 7, 2004, by J. Yeung and T. Yeung.

By re-supplying the disc cells with nutrients and oxygen through disc shunt or conduit, biosynthesis of sulfated glycosaminoglycans may increase to retain additional water and sustain compressive loading. In the presence of additional oxygen, production of lactic acid may decrease, minimizing acidic irritation, increasing production of ATP, and driving biosynthesis of the water-retaining proteoglycans. Hence, segmental instability and excessive loading of facet joints will be minimized to alleviate back pain.

Hypoxia is a potent stimulus for chronic inflammation by inducing macrophages and inflammatory cytokines. The intervertebral discs are the largest hypoxic tissue in the body. In painful discs, various inflammatory cytokines, including nitric oxide, interleukins, matrix metalloproteinases, prostaglandin E2 and tumor necrosis factor alpha are found. In fact, changes in nitric oxide levels in cerebrospinal fluid from pre- to post-surgery can be a quantitative predictor of surgical outcome in pain relief.

Location of pain source is hard to fully identify and frequently puzzling. Even in the presence of sciatica, MRI often fails to show compression of neural structures. The pain may be caused by leakage of inflammatory cytokines or lactic acid from the hypoxic disc to adjacent nerve spreading the pain sensation over several spine levels.

Discs L4-5 and L5-S1 are shielded by the ilium, inaccessible by straight needle from outside to deliver the conduit into the disc. However, through the pedicle of the vertebral body, the elastically curved needle proposed in PCT/US2005/022749 (US national 11/630,706), filed on Jun. 22, 2005 by J. Yeung, can puncture through the calcified endplate to deliver the shunt or conduit for exchange of nutrients and lactate between the avascular disc and body circulation.

Coating of immuno inhibitors was also proposed in PCT/US2007/03194 (US national Ser. No. 12/223,370) filed on Feb. 5, 2007 by J. Yeung and T. Yeung on the U-shaped disc shunt. Immuno inhibitor can be coated or incorporated into the shunts to minimize fibrous formation or tissue response.

SUMMARY OF INVENTION

A Quincke tipped introducer needle contains two shafts with lumens, one recessed, both connected by a slit for housing a U- or V-shaped disc shunt. The recessed shaft minimizes the penetration size of the introducer needle for insertion into a narrow and nerve laden space adjacent to a degenerated intervertebral disc. The longitudinal slit connecting the two lumens allows passage of the distal portion of the U-shaped disc shunt through the introducer needle, to be delivered into the intervertebral disc.

Pain emitting from the avascular disc is extremely difficult to treat due to lack of penetration or permeability of drug. The lumens of the introducer needle are also used to retain a peri-shunt injectable into the disc shunt for delivery into the painful disc. The peri-shunt injectable can be an analgesic, narcotic, anti-inflammatory drug, antibiotic, anticonvulsant, antidepressant, buffer agent or alkaline agent to alleviate pain. The peri-shunt injectable can also be a nerve toxin retained within the lumens to be loaded within the shunt for terminating transmission of pain signal emitting from the disc.

Back pain can also originate from the overloaded facet joints due to substantial decrease in disc height. The peri-shunt injectable can be a nutrient or growth factor to rebuild disc matrix and disc height. Hence, the compressive load will be therapeutically shifted from the strained facet joints to the repaired disc to alleviate facet loading and pain.

REFERENCE NUMBERS

100 Disc
101 Shunt-delivery needle
123 Spinal cord
126 Main disc shunt
128 Nucleus pulposus
129 Facet joint
159 Vertebral body
194 Nerve or spinal nerve
230 Introducer needle
269 Lumen of the shunt-delivery needle
373 Linked or attached shunt
430 Slit between the first and second lumens
431 First lumen of the introducer needle
432 Second lumen of the introducer needle
440 Recess or step of the introducer needle
441 Trocar
442 First rod of the trocar
443 Second rod of the trocar
444 Connector between the first and second rods of the trocar
445 Peri-shunt injection needle
446 Peri-shunt injectable or drug
447 Quincke point of the introducer needle
448 Quincke point of the trocar
450 Flat surface forming the Quincke point
451 Indentation of the trocar
452 Funnel
453 First funnel entry
454 Second funnel entry
455 Protrusion of funnel entries
456 Pointer or marker of the first funnel entry
457 Quincke point of the shunt-delivery needle
458 The first shaft of the introducer needle
459 The second shaft of the introducer needle

DETAILED DESCRIPTION OF THE EMBODIMENTS

In prior art, the disc shunt 126 was proposed to re-establish the exchange of waste and nutrients between the avascular disc 100 and body circulation. Drugs were proposed to coat the disc shunt 126 to enhance the pain relief or disc regeneration. Other drugs or chemicals were proposed to coat the disc shunt 126 to maintain open channels and performance of the disc shunt 126. In addition, the disc shunt 126 was proposed for transporting oral, intravenous, intra-muscular injection or general systemic drugs to treat inflammation or infection within the painful disc 100. Without the disc shunt 126, infusion of the systemic drugs into the avascular disc 100 would be insignificant, and the pain would persist.

In prior art, the U-shaped disc shunt 126 and linked shunt 373 were proposed to press-fit into the disc 100 to ensure preservation of the hydrostatic pressure of the disc 100, which is essential for preventing disc degeneration.

Figure 1:
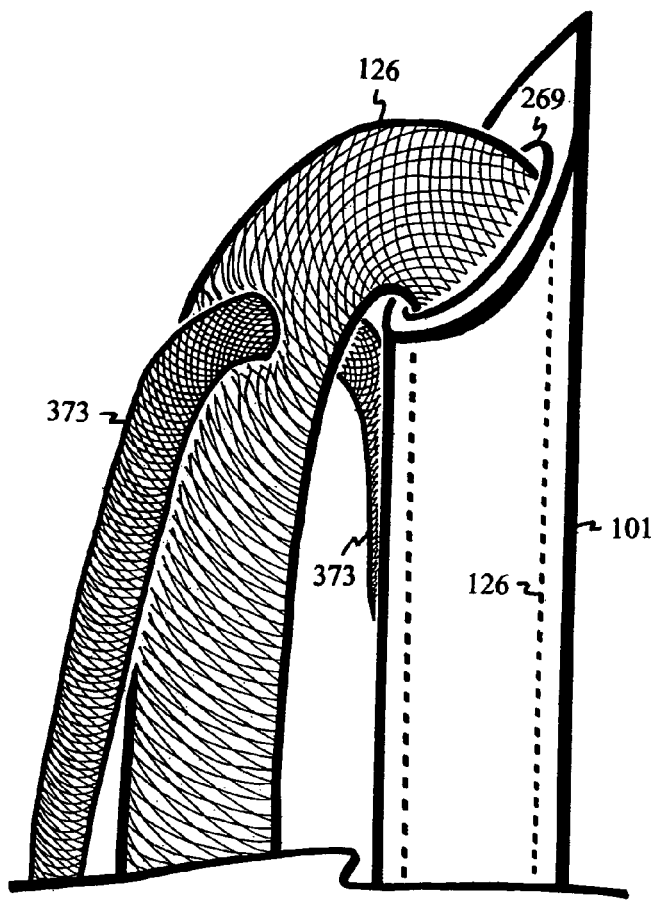
FIG. 1 (prior art) shows a U-shaped main disc shunt 126 extending from the lumen 269 of a shunt-delivery needle 101 and attaching to a linked shunt 373.

FIG. 1 (prior art) shows a main disc shunt 126 extending from the lumen 269 of the needle 101 and connecting to a linked shunt 373. The shunts 126, 373 are semi-permeable and porous, capable of transporting nutrients, oxygen and metabolites between the avascular disc 100 and body circulation. The shunts 126, 373 can also have capillary capability or action, drawing water from body circulation into the disc 100 to increase swelling pressure for sustaining compressive load. The shunts 126, 373 can be a braided thread, suture, sponge or a tube. The size of the capillary or porous channels ranges from 301 μm to 1 nm.

FIG. 1 (prior art) shows a linked shunt 373 threaded through or attached to the outside portion of the U-shaped main shunt 126. The combination of U-shaped main shunt 126 and linked shunt 373 increases mass to (1) allow rapid exchange of nutrients and waste between the degenerative disc 100 and body circulation, (2) seal and preserve hydrostatic disc 100 pressure, and/or (3) anchor within the disc 100 for deployment during needle 101 withdrawal.

Figure 2:
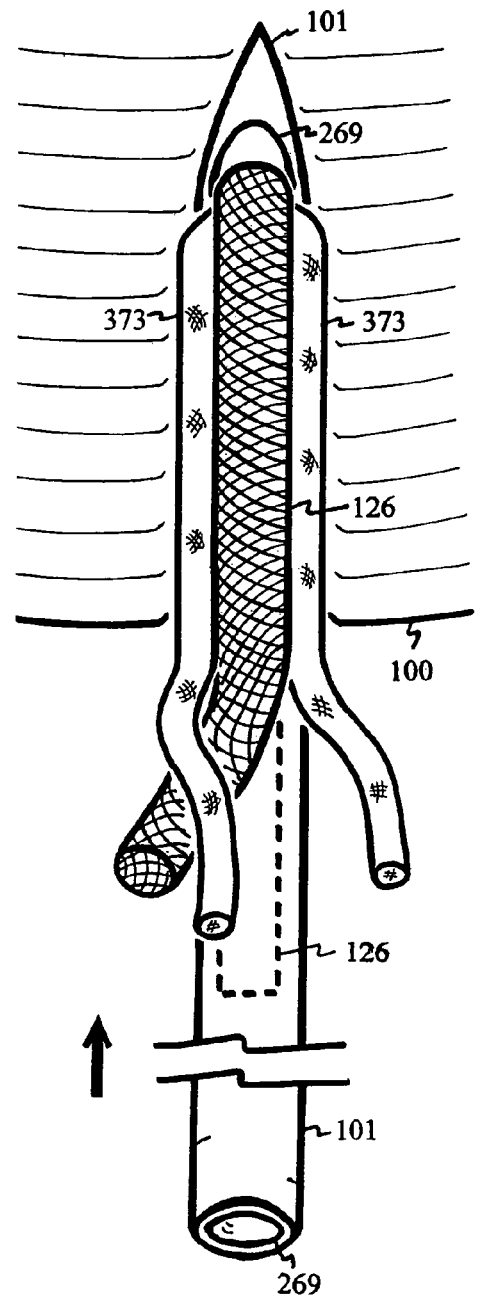
FIG. 2 (prior art) shows the shunt-delivery needle 101 puncturing and press-fitting the shunts 126, 373 into the disc 100 to preserve hydrostatic pressure.

FIG. 2 (prior art) shows the needle 101 delivering the shunt 126 and linked shunt 373 to press-fit into the annular layers and preserve hydrostatic pressure of the disc 100. The linked shunt 373 can attach anywhere along the outside portion of the main shunt 126. To position the sequential press-fit, attachment of the linked shunt 373 should be slightly behind or away from the U-loop or V-loop of the main shunt 126 to minimize shunt diameter at entry for disc 100 puncturing. In addition to aiding deployment of the main shunt 126, the linked shunt 373 provides additional sealing capacity within the annulus to preserve hydrostatic pressure of the repaired disc 100.

Figure 3:
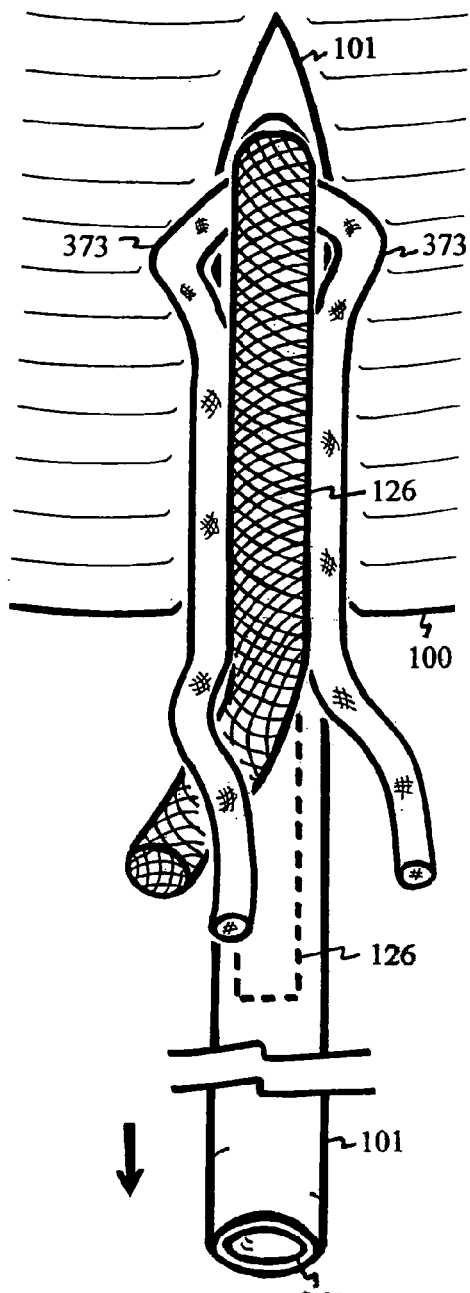
FIG. 3 (prior art) depicts the kinking or spreading of the linked shunt 373 to add friction between the linked shunt 373 and annulus during withdrawal of the needle 101.
Figure 4:
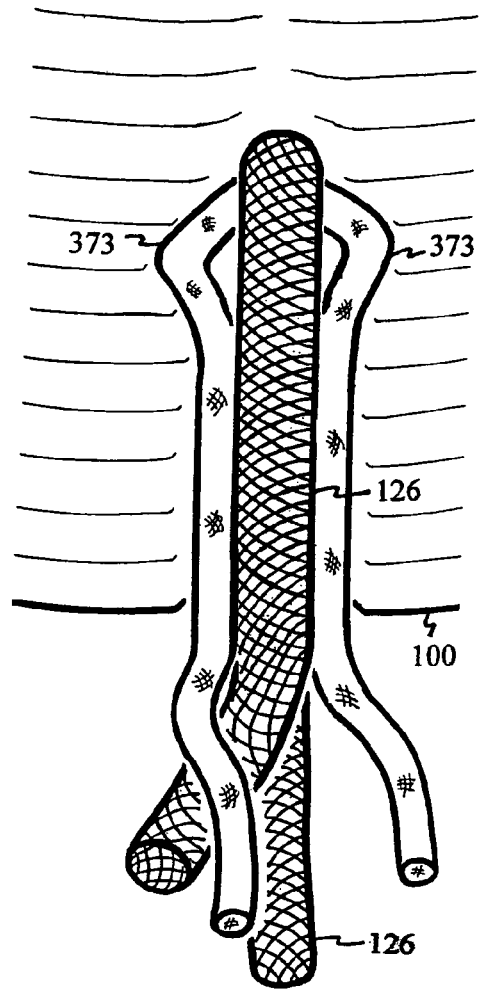
FIG. 4 (prior art) shows deployment of the main shunt 126 and linked shunt 373 by withdrawing the needle 101.
Figure 4:
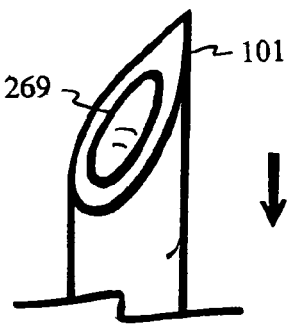

The linked shunt 373 is likely to buckle, kink, distort, shift or spread, adding friction between the linked shunt 373 and the disc 100 during needle 101 withdrawal, as shown in FIG. 3. Similar movement and friction may apply to the outside portion of the U-shaped main shunt 126. As a result, the inside portion of the main shunt 126 can slide out of the lumen 269 during needle 101 withdrawal to deploy both shunts 126, 373 as shown in FIG. 4, for re-establishing the exchange of waste and nutrients between the avascular disc 100 and body circulation. The deployed main 126 and linked 373 shunt can also transport drugs, oxygen, buffering agent or nerve toxin into the avascular disc 100 to alleviate back pain.

Figure 5:
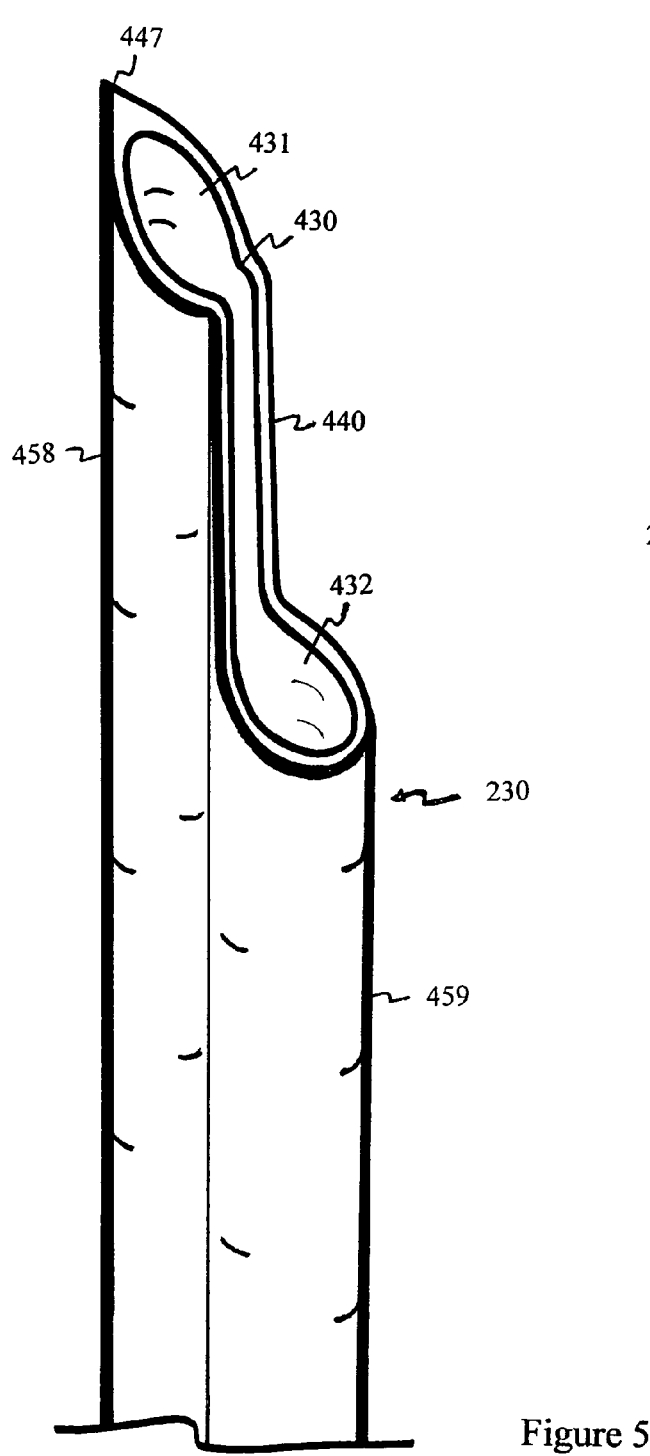
FIG. 5 shows a slit 430 opening between the first lumen 431 and second lumen 432 of the introducer needle 230.
Figure 6:
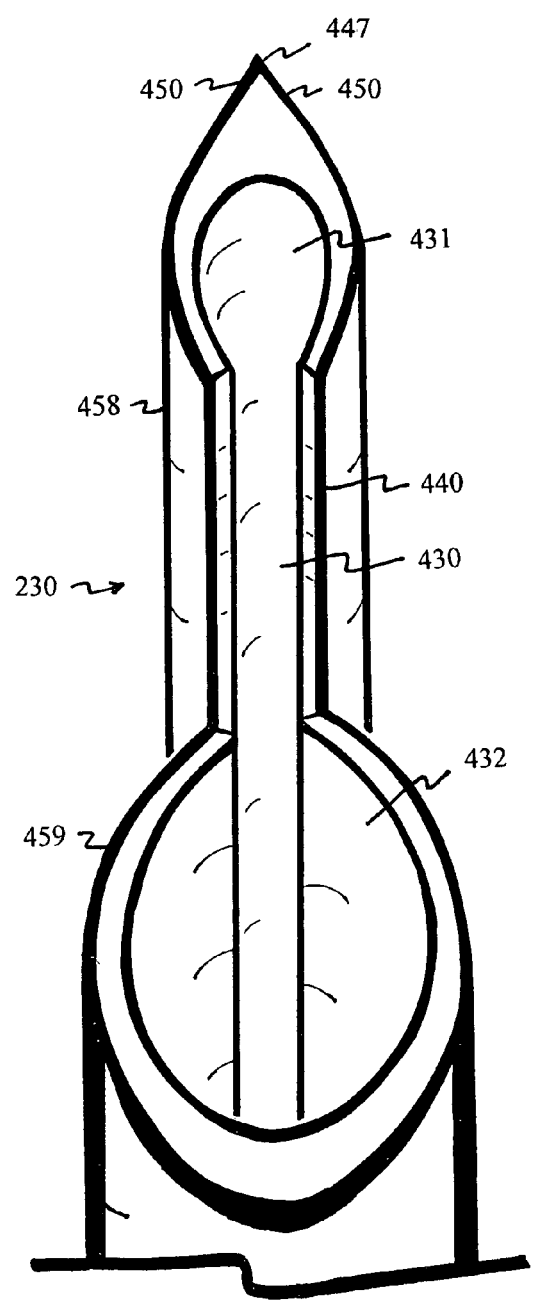
FIG. 6 shows a recess 440 at the distal end of the introducer needle 230 to form an extended first shaft 458 with a Quincke point 447 and a recessed second shaft 459.
Figure 7:
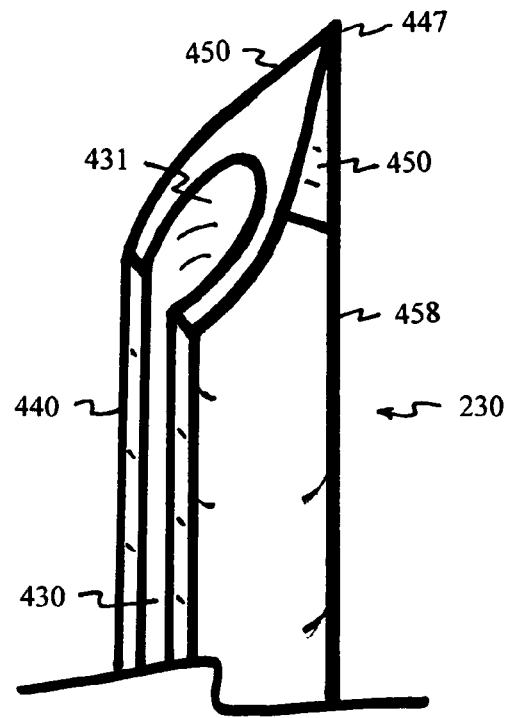
FIG. 7 shows a side view of the introducer needle 230 with a flat surface 450 sharpened to a Quincke point 447.
Figure 8:
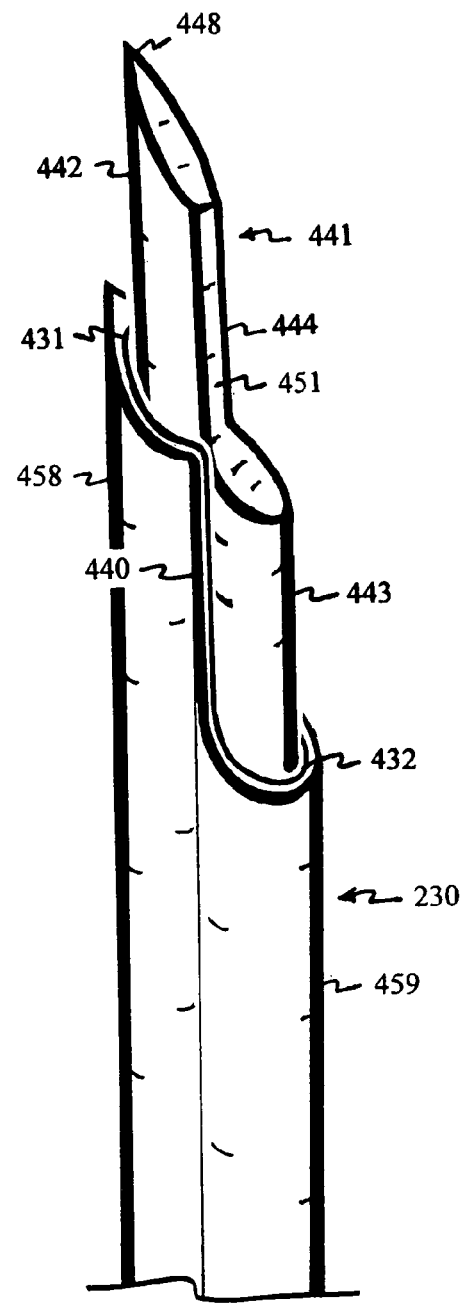
FIG. 8 shows a trocar 441 inside the introducer needle 230 with size, shape and indentation 451 matching the first lumen 431, second lumen 432 and recess 440.

Safe delivery of the disc shunts 126, 373 for treating the degenerated disc 100 is challenged by obstruction of nerves 194 and facet joints 129. The available area for needle 101 entry into the disc 100 is small. The distal portion of the introducer needle 230 is made small or thin with a recess 440 or step, by forming an extended first shaft 458, as shown in FIGS. 5 to 7, for entering between the nerve 194 and facet joints 129. A second shaft 432 is recessed at the distal portion of the introducer needle 230, as shown in FIGS. 5 and 6, to avoid contact with a network of nerves near the spine. The distal ends of both the first 458 and second 459 shafts are beveled to facilitate tissue puncturing, as shown in FIGS. 5, 6 and 8. In addition, the distal tip of the first shaft 458 is sharpened by laterally flattened surfaces 450 into a Quincke point 447, as shown in FIGS. 6 and 7. The Quincke point 447, 448, 457 for implanting disc shunts 126, 373 contains blunt surfaces adjacent to the sharp tip for tissue puncturing. The Quincke point 447, 448, 457 is tapered and formed by non-blade-like surfaces or edges for puncturing and penetration into tissue with minimal tissue incision to reduce the possibility of severing nerves 194. A first lumen 431 of the first shaft 458 and a second lumen 432 of the second shaft 459 join or overlap to form a longitudinal slit 430 or opening, as shown in FIGS. 5 and 6. The first lumen 431, second lumen 432 and slit 430 are open from the proximal end to distal end of the introducer needle 230.

A trocar 441 has a connector 444 portion between a first rod 442 and a second rod 443, as shown in FIG. 8. An indentation 451 is formed by recessing the second rod 443 of the trocar 441. The distal ends of the first 442 and second rod 443 are beveled to facilitate tissue puncturing. The distal tip of the first rod 442 is sharp for tissue penetration, preferred to be a Quincke point 448 to minimize potential incision of nerves.

Figure 9:
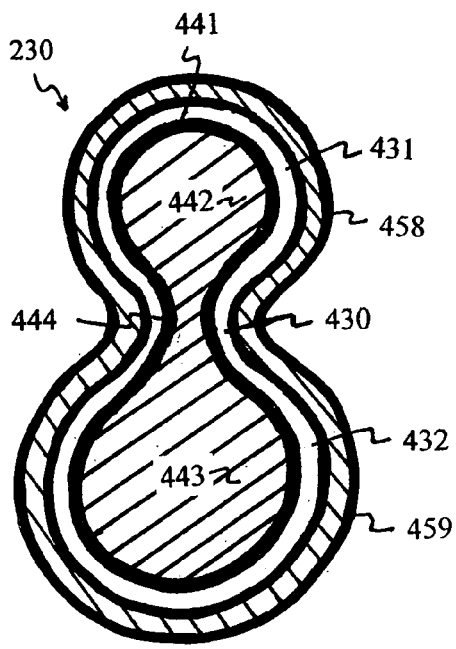
FIG. 9 shows a cross-section of the trocar 441 within the introducer needle 230.

The cross-section of the trocar 441 is sized and configured to fit within the first lumen, second lumen and slit of the introducer needle 230, as depicted in FIG. 9. The first rod 442 of the trocar 441 fits within the first lumen 431 of the introducer needle 230. The second rod 443 fits within the second lumen 432. The connector 444 fits within the slit 430. Hence, the trocar 441 can slide freely within the introducer needle 230, and the introducer needle 230 can slide freely over the trocar 441. The trocar 441 and introducer needle 230 are stiff enough to puncture tissue, but flexible enough to bend and direct toward the disc 100 by a physician or operator. The trocar 441 and/or the introducer needle 230 can be made with nickel-titanium alloy, stainless steel, titanium or polymers.

Figure 10:
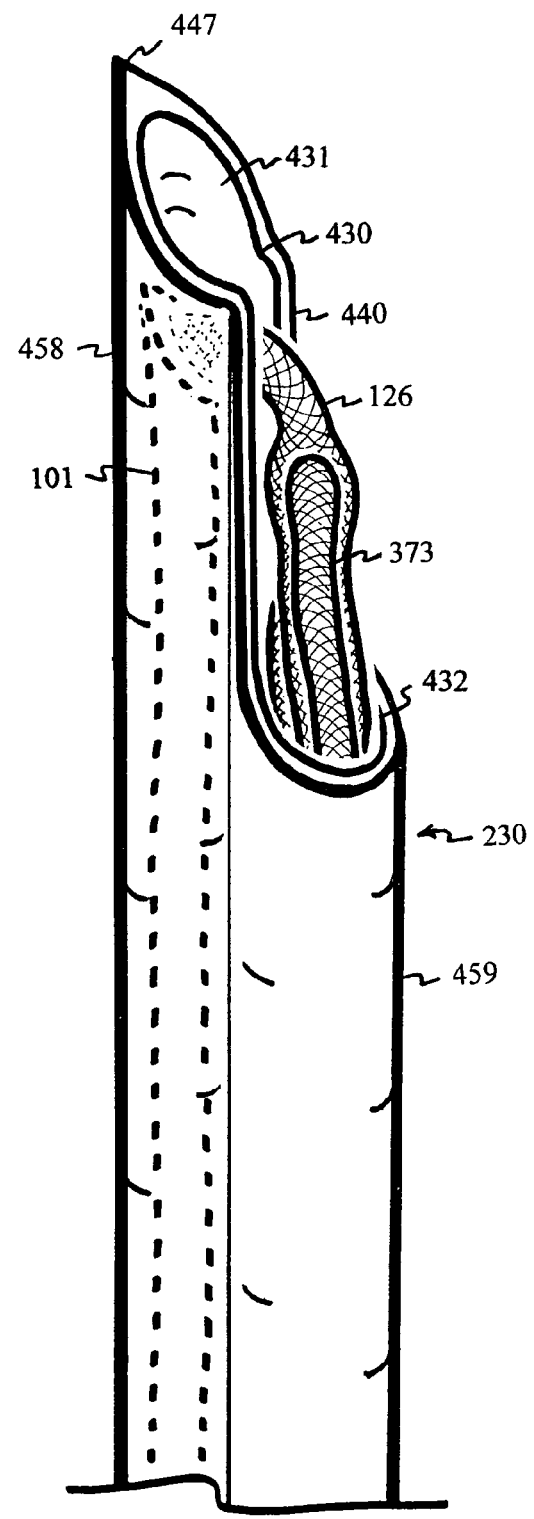
FIG. 10 shows the shunt-delivery needle 101, main shunts 126 and linked shunt 373 within the first 431 and second 432 lumens of the introducer needle 230.

After reaching the disc 100, the trocar 441 is replaced by the shunt-delivery needle 101 loaded with shunts 126, 373 into the introducer needle 230. The shunt-delivery needle 101 is inserted into the first lumen 431. The main shunt 126 extends from the first lumen 431 of the introducer needle 230 and passes through the slit 430 to pull the linked shunt 373 into the second lumen 432, as shown in FIG. 10. The first proximal end of the main shunt 126 is housed within the first lumen 431. The second proximal end of the main shunt 126 and both proximal ends of the linked shunt 373 are housed within the second lumen 432. The distal portion of the disc shunt 126 is within the slit 430 of the introducer needle 230. The housing separation of the shunts 126, 373 allows safe delivery using the thin first shaft 458 through a dense network of nerves around the disc 100.

Infection within the avascular disc 100 can cause severe back pain and is difficult to treat. The shunts 126, 373 are made with material for absorbing fluid and can be easily contaminated. The introducer needle 230 shields the shunts 126, 373 from contacting the skin or epidermis layers of the patient, which can be contaminated with bacteria or virus, causing infection within the disc 100. The first proximal end of the main shunt 126 is housed within the first lumen 431 of the introducer needle 230. The second proximal end of the main shunt 126 and the linked shunt 373 are housed within the second lumen 432. The distal portion of the disc shunt 126 is housed within the slit 430, as shown in FIG. 10, to shield from potential contamination.

Figure 11:
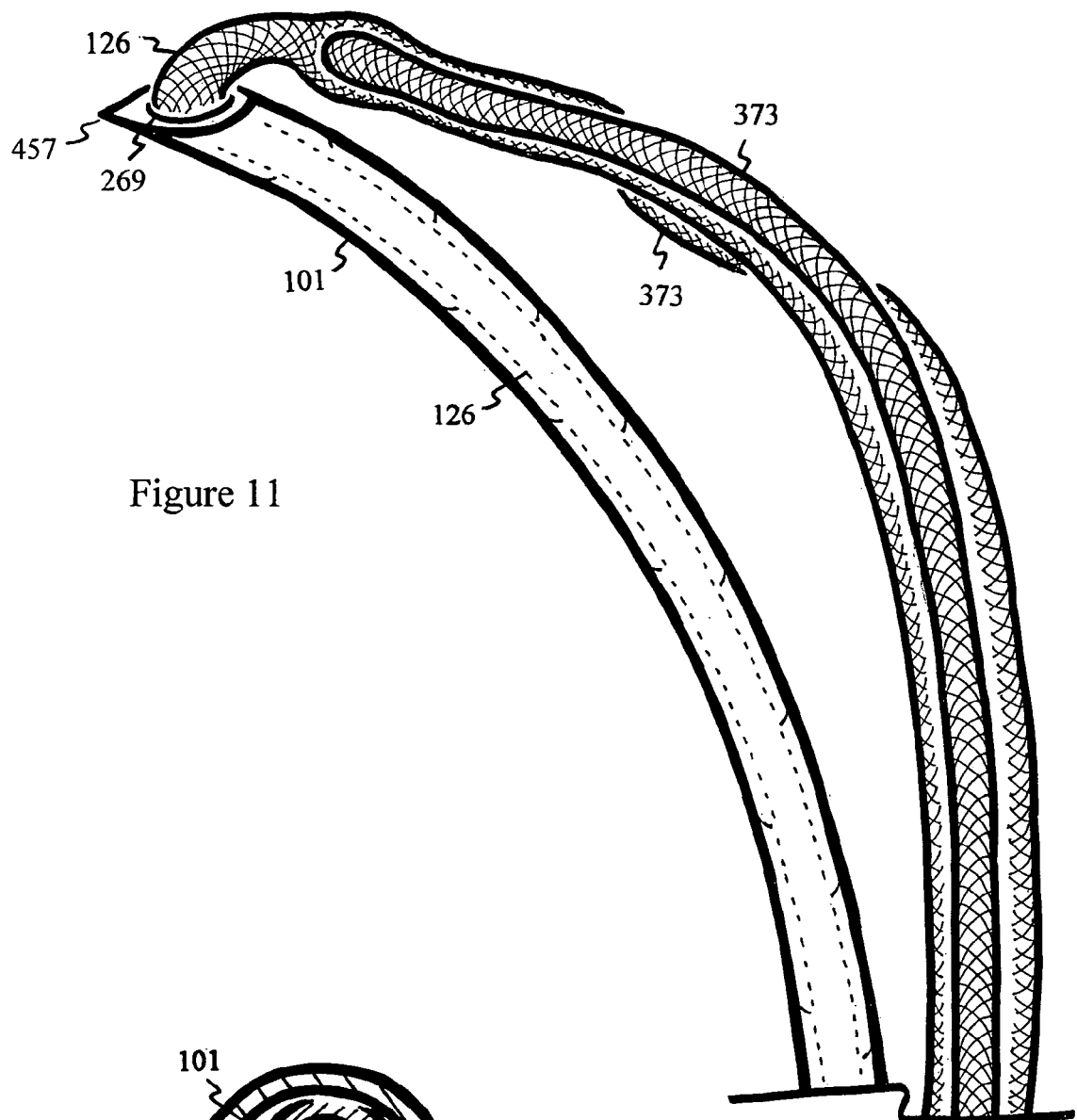
FIG. 11 shows a main disc shunt 126 extending from the lumen 269 of a curved shunt-delivery needle 101.
Figure 12:
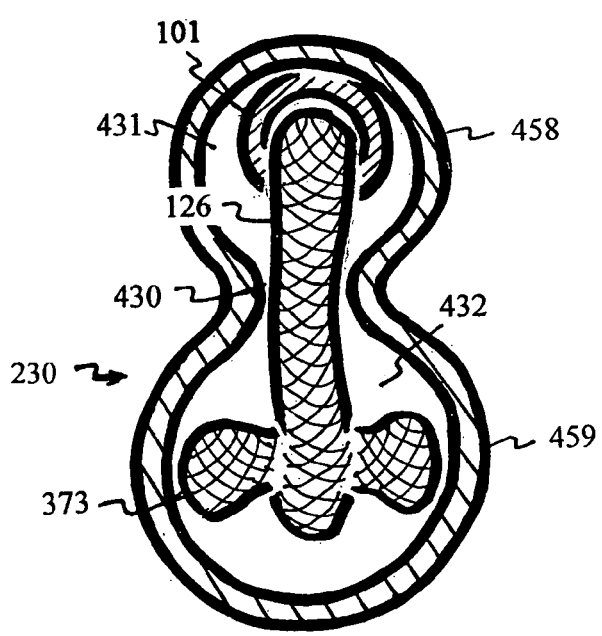
FIG. 12 shows a cross-section of the shunt-delivery needle 101, introducer needle 230, slit 430 and loaded main shunt 126 and linked shunt 373 within the first 431 and second 432 lumens.
Figure 13:
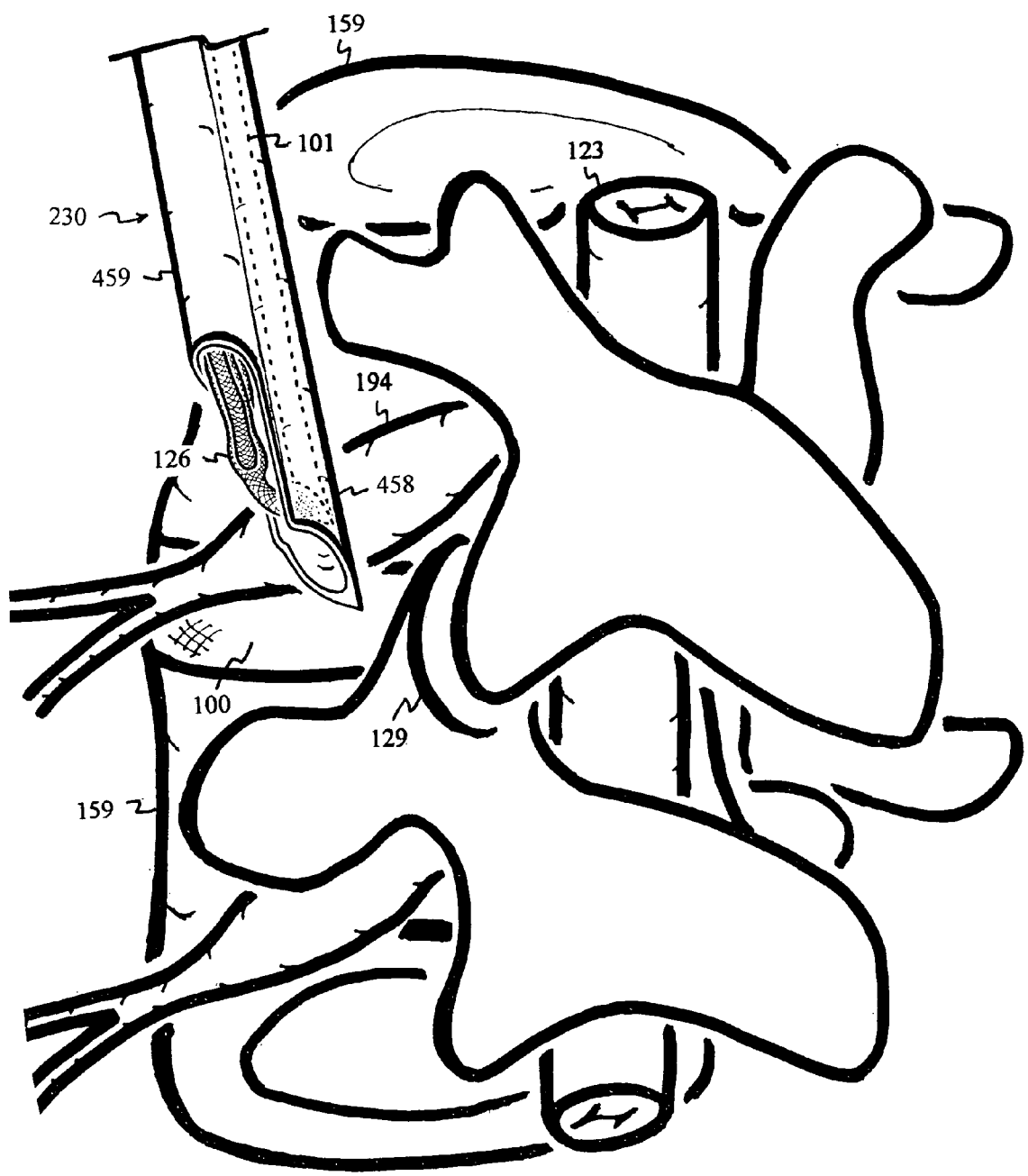
FIG. 13 shows the extended first shaft 458 penetrating through a crowded space between nerve 194 and facet joint 129 to deliver the disc shunt 126 to the disc 100.

The lower lumbar discs, L4-5, L5-S1, are shielded by the ilium, inaccessible by straight-needle puncturing. A curved shunt-delivery needle 101, as shown in FIG. 11, provides an angle or direction for puncturing toward the center of the disc 100. The shunt-delivery needle 101 can be made with a resilient or super elastic material, such as nickel-titanium alloy, spring steel or other. The puncturing tip of the shunt-delivery needle 101 is a Quincke point 457, as shown in FIG. 11, to minimize potential damage to nerves 194. The outer diameter of the shunt-delivery needle 101 is larger or wider than the slit 430 of the introducer needle 230, but is smaller or thinner than the inner diameter of the first lumen 431 of the introducer needle 230. Hence, the shunt-delivery needle 101 is resiliently straightened within the first lumen 431, incapable of passing or protruding through the slit 230 to rub or damage the extended portion of the main shunt 126 and linked shunt 373 within the second lumen 432 of the introducer needle 230. FIGS. 10 and 12 show separate housing for the resiliently straightened shunt-delivery needle 101 in the first lumen 431 and the extended portion of the main shunt 126 and linked shunt 432 in the second lumen 432 of the introducer needle 230. The first shaft 458 of the introducer needle 230 can be quite small, relative to the size of the entire introducer needle 230, as depicted in FIG. 12, for penetrating a crowded space. The recessed second shaft 459 avoids contact with vulnerable nerves 194, as depicted in FIG. 13.

The length of the recess 440 or step ranges between 1 and 7 cm, but preferably between 1.5 and 3 cm. The diameter of the first lumen 431 ranges between 0.5 and 4 mm, but preferably between 0.6 and 3 mm. The width of the slit 430 ranges between 0.1 and 2.5 mm, but preferably between 0.4 and 1 mm. The diameter of the second lumen 432 ranges between 0.5 and 5 mm, but preferably between 0.7 and 3 mm.

Figure 14:
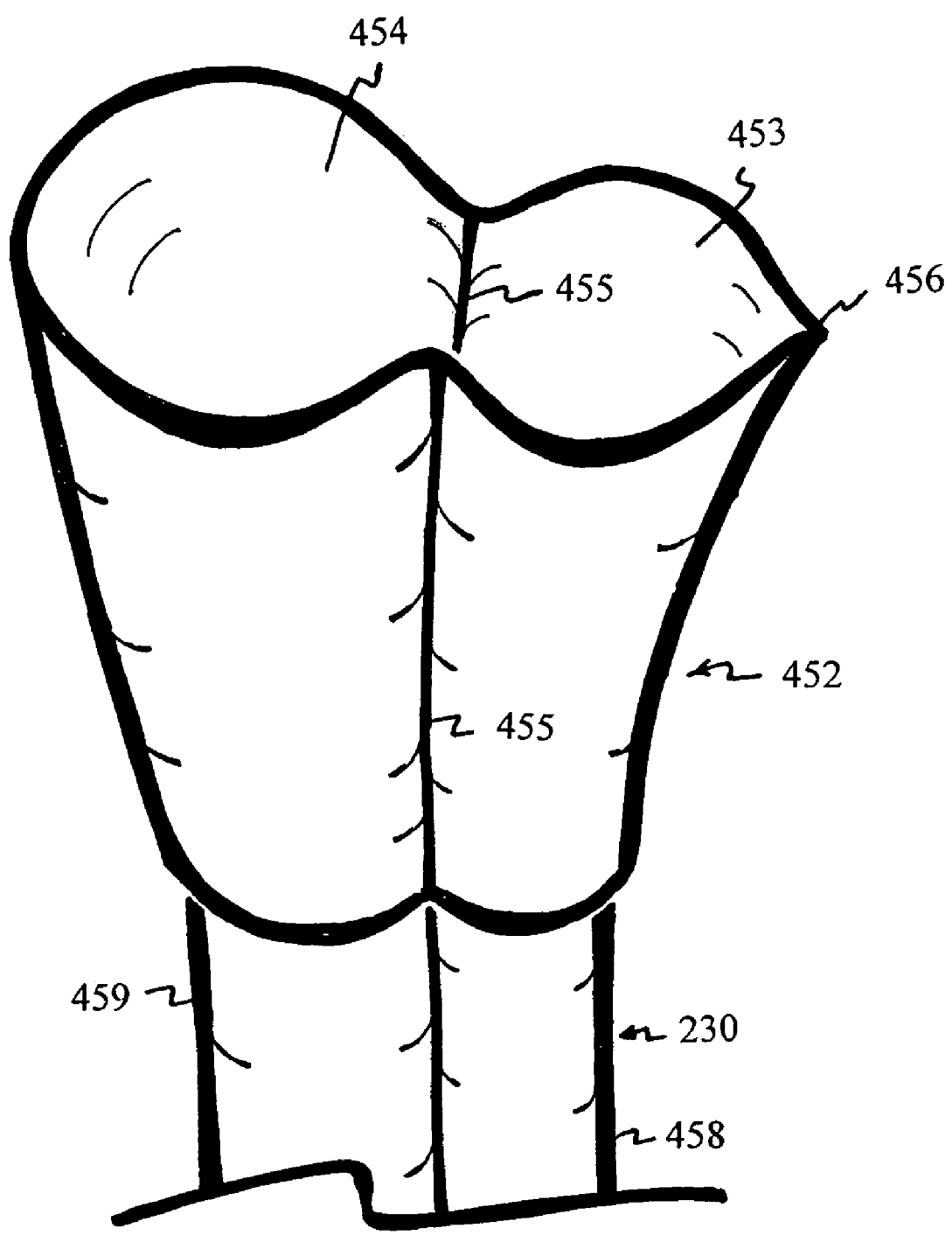
FIG. 14 shows a funnel 452 to assist insertion of the shunt-delivery needle 101.

A funnel 452 provides enlarged entries to assist insertion of the shunt-delivery needle 101 into the small first lumen 431. The funnel 452 at the proximal end of the introducer needle 230, as shown in FIG. 14, contains a first funnel entry 453 channeling into the first lumen 431, a second funnel entry 454 channeling into the second lumen 432 and two protrusions 455 guiding the main shunt 126 into the slit 430 of the introducer needle 230. The distal end of the funnel 452 has a ledge to fit over the first 458 and second 459 shafts of the introducer needle 230, for a smooth surface transition between the funnel entries and lumens. The funnel 452 has a marker or pointer 456 at the first funnel entry 453, as shown in FIG. 14, visible by the operator or physician for insertion of the shunt-delivery needle 101 into the first lumen 431 of the introducer needle 230. The extended portion of the main shunt 126 is guided by the protrusions 455 into the slit 430. The linked shunt 373 is guided through the second funnel entry 454 into the second lumen 432 of the introducer needle 230. The funnel 452 is removable from the proximal end of the introducer needle 230.

Figure 15:
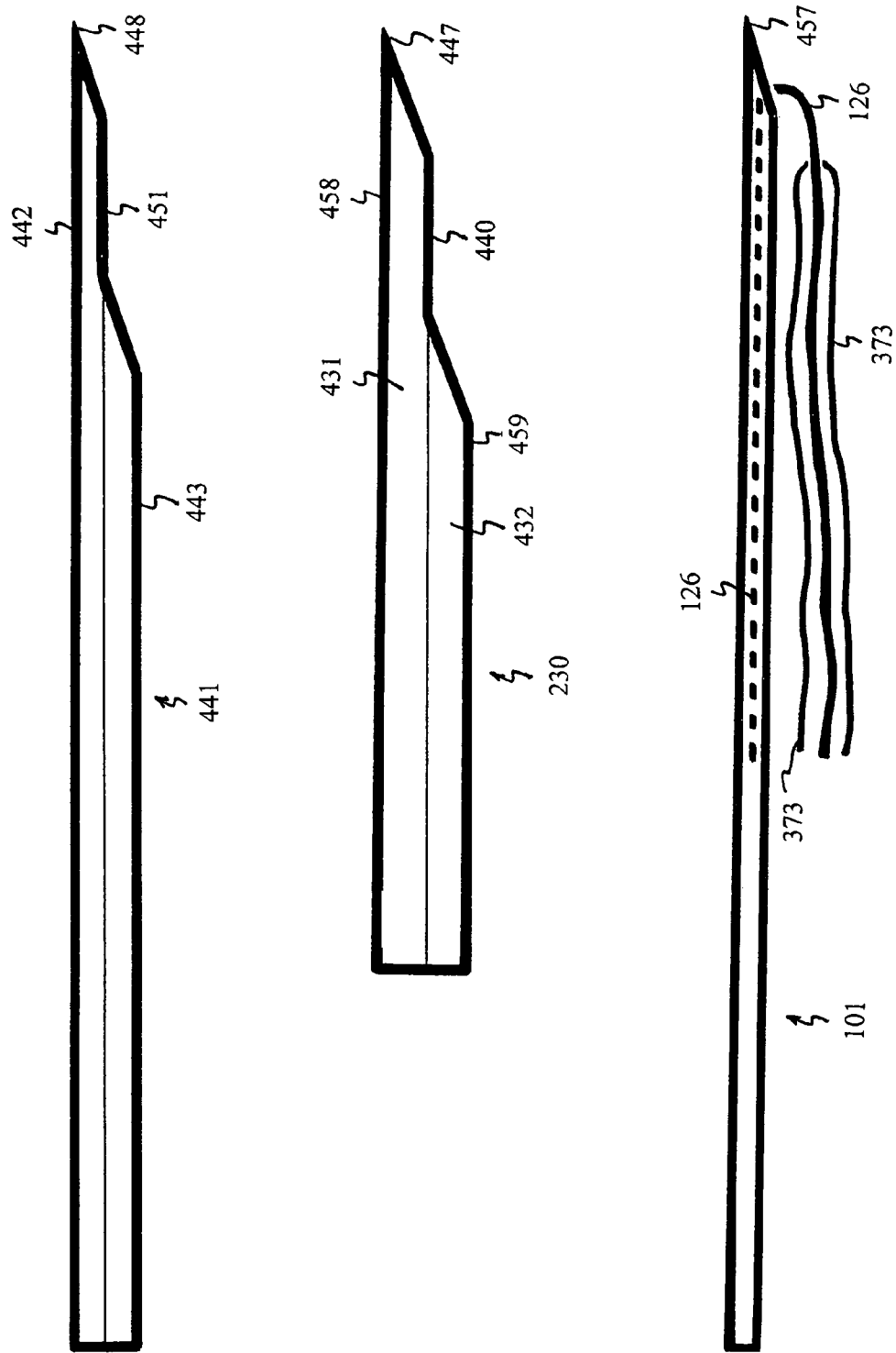
FIG. 15 shows relative lengths of the trocar 441, introducer needle 230, shunt-delivery needle 101, main shunt 126 and linked shunt 373 for the implant procedure.

Relative lengths of the trocar 441, introducer needle 230 and shunt-delivering needle 101, as depicted in FIG. 15, are essential for implanting the shunts 126, 373 to treat the degenerated disc 100. The distal ends of the trocar 441, introducer needle 230 and shunt-delivering needle 101 are beveled and Quincke pointed. The trocar 441 is longer than the introducer needle 230 to expose the proximal end of the trocar 441 for withdrawal from the introducer needle 230. Additional introducer needles can be used to dilate tissue before insertion of the shunt-delivery needle 101. A second introducer needle is larger but shorter than the original or the first introducer needle 230. The second introducer needle is sized and configured to fit and slide over the original or the first introducer needle 230. A third or a fourth introducer needle can be used to sequentially dilate the tissue before insertion of the shunt-delivery needle 101. Sequential dilations can reduce the potential of nerve damage and minimize discomfort of the patient. The original or the first introducer needle 230 is longer and thinner than the second introducer needle, and the second introducer needle is longer and thinner than the third and subsequent introducer needles. The trocar 441 and shunt-delivery needle 101 are longer than the first introducer needle 230 and each subsequent introducer needle 230.

For implantation of disc shunts 126, 373, the patient is placed prone on a radiolucent operating table. The trocar 441 and introducer needle 230 puncture through sterilely prepped skin. Guided by the anterior/posterior and lateral images of the fluoroscope, the trocar 441 and introducer needle 230 are positioned and advanced by a physician or operator toward the degenerated disc 100. When the trocar 441 and introducer needle 230 reach the surface of the disc 100, the trocar 441 is replaced by the shunt-delivery needle 101 into the first lumen 431 of the introducer needle 230.

Figure 16:
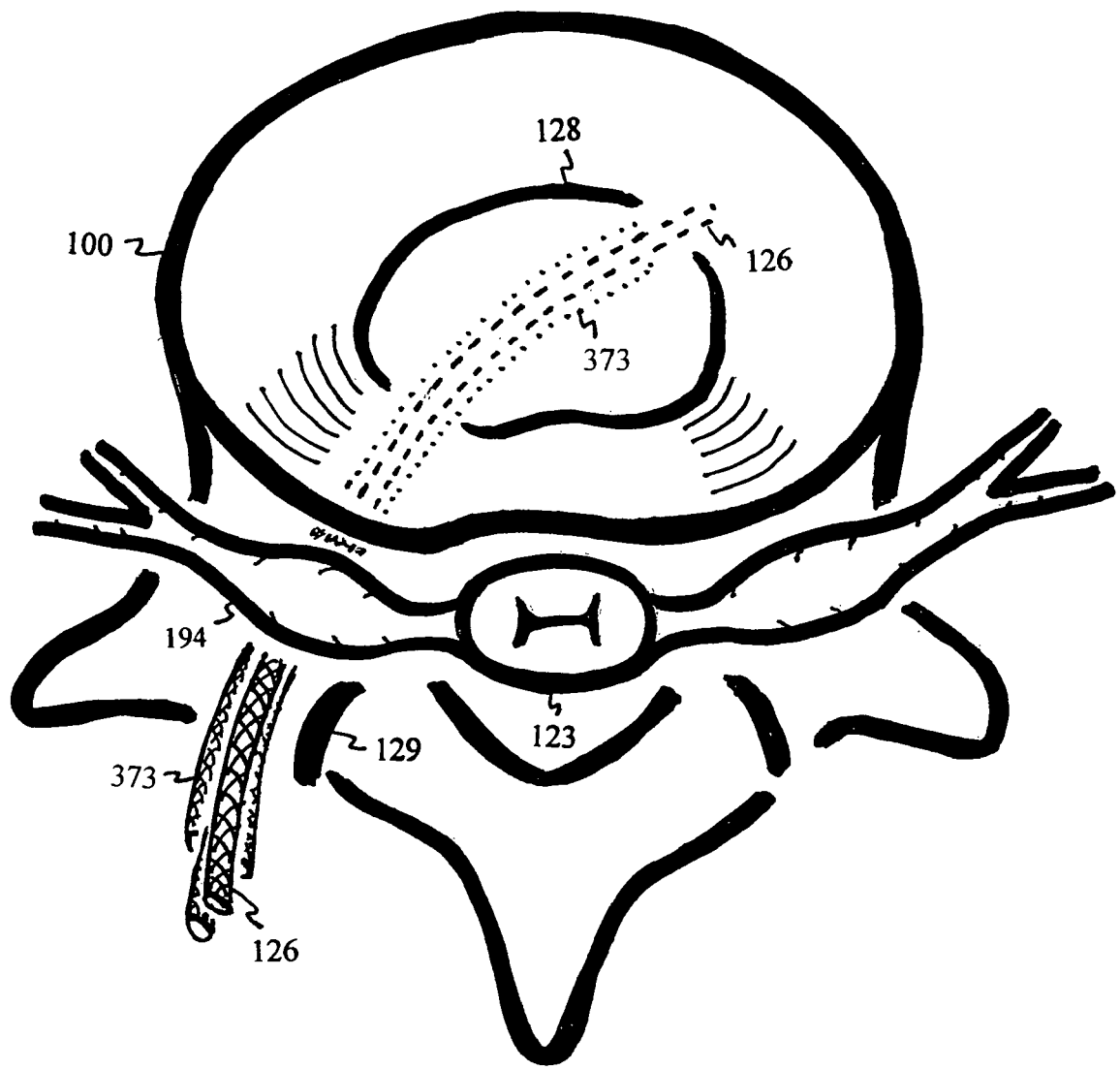
FIG. 16 shows the main shunt 126 and linked shunt 373 bridging between the avascular disc 100 and adjacent tissue for body circulation.

The shunt-delivery needle 101, carrying the shunts 126, 373 through the introducer needle 230, punctures into the disc 100. The shunts 126, 373 are press-fitted into the disc 100 with significant friction. The friction is essential to holding the press-fitted shunts 126, 373 stationary while the shunt-delivery needle 101 is withdrawn to deploy the shunts 126, 373 in the disc 100, as shown in FIG. 16.

Most back pain starts with a degenerated disc 100. In fact, the pain of many patients is emitted from the disc 100, verifiable as concordant pain during discography. The pain may be caused by inflammation, infection, lactic acid irritation, nerve ingrowth, annular derangement, chemical imbalance, hyper-sensitized nerve or other reasons. Due to the avascular nature of the disc 100, systemic drugs cannot circulate into the disc 100 to treat the malady and pain. Hence, disc pain often persists to torment the patients.

Drugs can be injected at, over or adjacent to the shunts 126, 373. The drugs permeate the shunts 126, 373 into the degenerated disc 100 to treat the malady causing the pain. Otherwise, the malady continues, and the pain persists. Injection over or around the disc shunts 126, 373 is called peri-shunt injection for infusing injectable 446 or drug into the shunts 126, 373. Peri-shunt injection into tissue can form a bolus or reservoir of drugs 446 within the tissue. Peri-shunt injection can be done concurrently during shunts 126, 373 implantation, or during follow-up visit to further treat the back pain.

Figure 17:
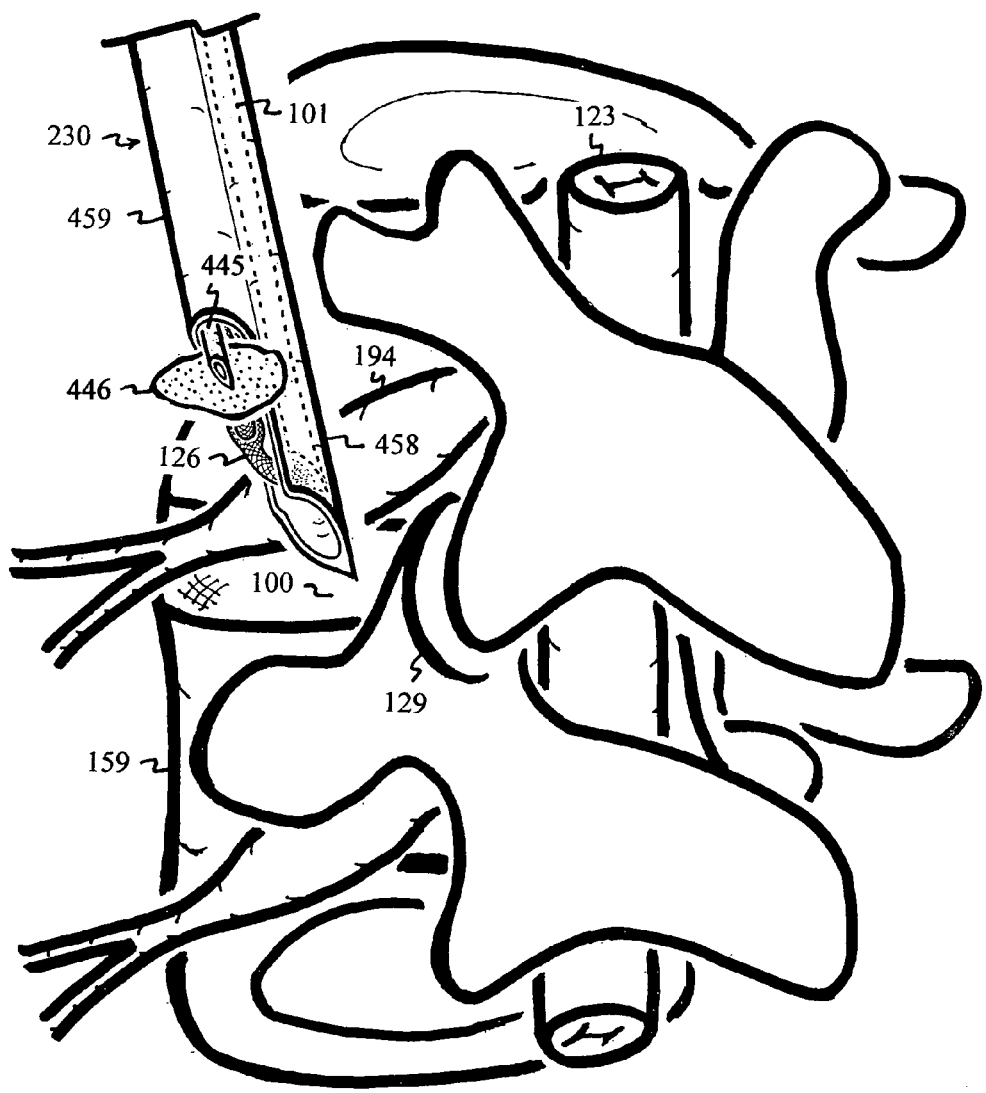
FIG. 17 shows a peri-shunt injection needle 445 through the second lumen 432 of the introducer needle 230 to deliver an injectable 446 to the shunts 126, 373 and surrounding tissue.

A peri-shunt injection needle 445 extends from the second lumen 432 of the second shaft 459 of the introducer needle 230 to inject an injectable or drug 446, as shown in FIG. 17. Many cases of back pain are caused by lactic acid irritation or inflammation within and/or adjacent to the disc 100. The injectable 446 can be a buffer, alkaline or anti-inflammatory agent to treat the acid burn or inflammation. The peri-shunt injection needle 445 is longer than or equal to the length of the second shaft 459, but shorter than the first shaft 458 of the introducer needle 230. Hence the injectable 446 can alleviate pain in the surrounding tissue and simultaneously load the shunts 126, 373 before puncturing and delivering into the disc 100 for pain relief, as shown in FIG. 17.

Figure 18:
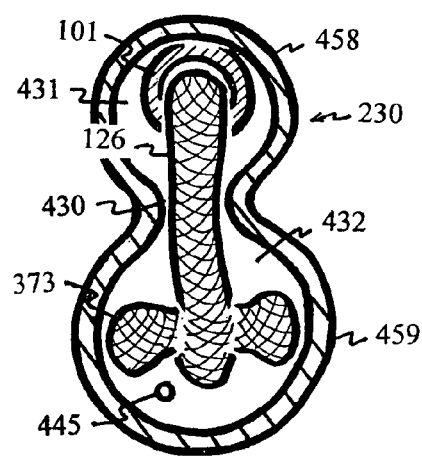
FIG. 18 shows a cross-section of a peri-shunt injection needle 445 within the second lumen 432 of the introducer needle 230.

The peri-shunt injection needle 445 can be made shorter than the second shaft 459 of the introducer needle 230. FIG. 18 shows a peri-shunt injection needle 445 within the cross-section of the second lumen 432 of the introducer needle 230. The injectable 446 is retained and absorbed by the shunts 126, 373 within the second lumen 432 of the introducer needle 230. Retaining the injectable 446 within the second lumen 432 is highly significant if the injectable 446 is a nerve toxin, such as BOTOX®, to avoid or minimize toxic exposure to the spinal nerve 194. After loading the nerve toxin or other injectable 446, the shunts 126, 373 are delivered into the disc 100. Degenerated discs 100 are usually relatively dry and will quickly draw the injectable 466 within the shunts 126, 373 along with fluid tapped from the adjacent tissue into the disc 100.

Figure 19:
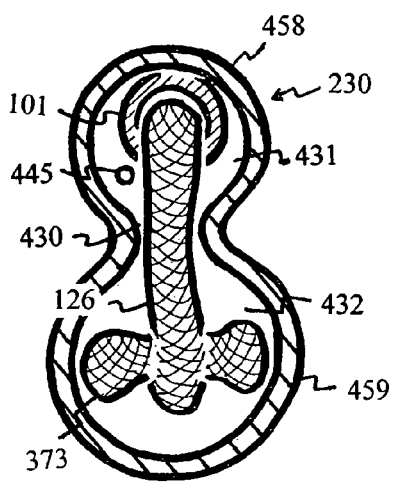
FIG. 19 shows a cross-section of the peri-shunt injection needle 445 within the first lumen 431 of the introducer needle 230.

Similarly, the peri-shunt injection needle 445 can be inserted into the first lumen 431. The injectable 446 permeates through the slit 430 to be loaded on the shunts 126, 373 in the second lumen 432, as shown in FIG. 19.

Figure 20:
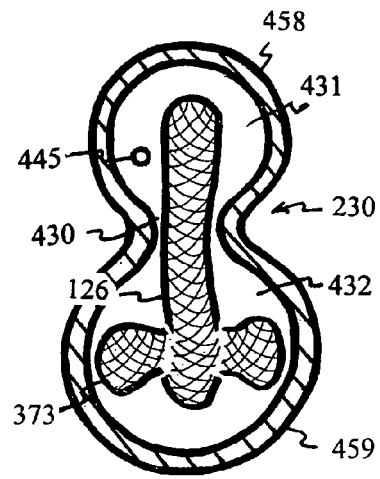
FIG. 20 shows a cross-section of the injection needle 445 in the first lumen 431 of the introducer needle 230, after withdrawal of the shunt-delivery needle 101.
Figure 21:
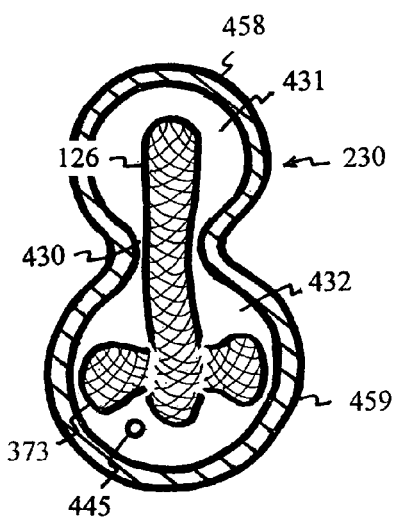
FIG. 21 shows a cross-section of an injection needle 445 in the second lumen 431 of the introducer needle 230, after withdrawal of the shunt-delivery needle 101.

Peri-shunt injection 446 can also be done after deployment of the shunts 126, 373 by withdrawing the shunt-delivery needle 101. The proximal ends of the shunts 126, 373 are still within the lumens 431, 432 of the introducer needle 230. The peri-shunt injection needle 445 can be inserted into the first lumen 431, as shown in FIG. 20, or into the second lumen 432 of the introducer needle 230 as shown in FIG. 21. The first 431 and second 432 lumens of the introducer needle 230 retain the injectable or drug 446 to be drawn by the shunts 126, 373 into the degenerated disc 100. The length of the peri-shunt injection needle 445 is shorter than the length of the first shaft 458, and preferred to be shorter than the second shaft 459 of the introducer needle 230. Due to the controlled length of the peri-shunt injection needle 445, fluoroscopic guidance is not required for peri-shunt injection through the introducer needle 230.

Figure 22:
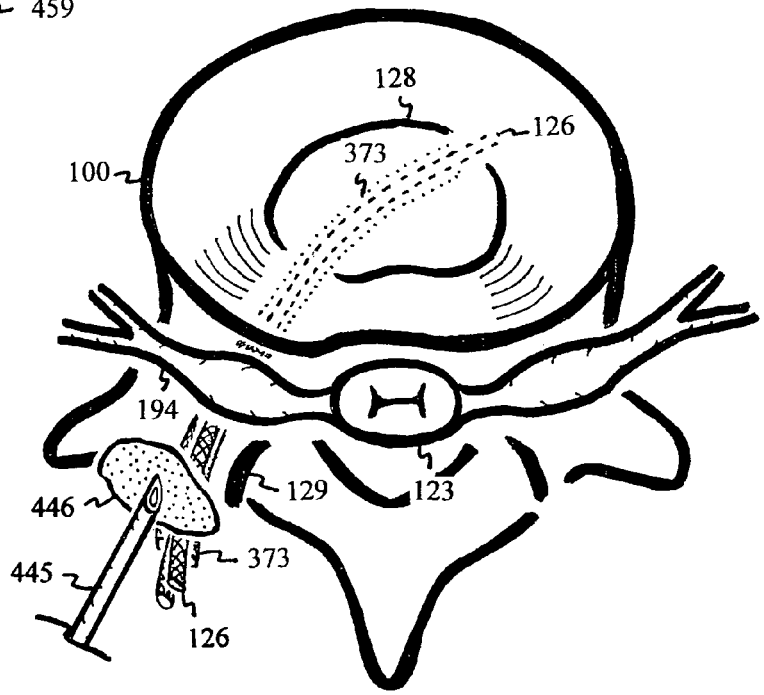
FIG. 22 shows a peri-shunt injection 446 after withdrawal of the introducer needle 230.

After implantation of the shunts 126, 373, the patient can return for additional peri-shunt injections, as shown in FIG. 22. The tip of the peri-shunt injection needle 445 is also Quincke pointed to minimize potential damage to the nerve 194. Peri-shunt injection can be done with or without fluoroscopic guidance, but fluoroscopic guidance is preferred to inject the peri-shunt injectable 446 near the disc 100 to enhance the effectiveness of the injectable 446. A bolus of injectable or drug 446 may be deposited as a reservoir in tissue to be drawn by the disc shunts 126, 373 into the disc 100.

The introducer needle 230, trocar 441, shunt-delivery needle 101, peri-shunt injection needle 445 can be flexible and/or coated with a lubricant, radiopaque, echogenic, or image-enhancing coating to improve operation and/or visibility.

The peri-shunt injectable 446 can be an analgesic, narcotic, anti-inflammatory drug, antibiotic, muscle relaxant, anticonvulsant, antidepressant, buffer agent, alkaline agent or calcium channel blocker to alleviate or reduce pain. The peri-shunt injectable 446 can be a nerve toxin to terminate transmission of pain signal. The peri-shunt injectable 446 can be a nutrient to rebuild disc 100 matrix and disc height for reduction of pain from facet loading or spinal stenosis. The peri-shunt injectable 446 can be a growth factor to regenerate the degenerated disc 100. The peri-shunt injectable 446 can be an inhibitor of fibrous formation to prevent or minimize encapsulation over the shunts 126, 373. The peri-shunt injectable 446 can be an anti-angiogenic factor to prohibit ingrowth of blood vessel and/or nerve into the disc 100. The peri-shunt injectable 446 can also be a chemotherapy drug to treat tumor within the spine.

The peri-shunt injectable 446 can be an analgesic, such as bupivacaine, lidocain, ketorolac, Sarapin® or other, to treat the pain within and around the disc 100.

The peri-shunt injectable 446 can be an opioid or narcotic, such as fentanyl, methadone, morphine, oxycodone, propoxyphene, meperidine, hydromorphone, codeine, hydrocodone, or other, to reduce the intense pain.

The peri-shunt injectable 446 can be an inhibitor of cyclooxygenases, such as aspirin (acetylsalicylic acid or 2-acetoxybenzoic acid), ibuprofen (iso-butyl-propanoic-phenolic acid), naproxen [(+)-(S)-2-(6-methoxynaphthalen-2-yl) propanoic acid], celecoxib {4-[5-(4-methylphenyl)-3-(trifluoromethyl)pyrazol-1-yl]benzenesulfonamide}, rofecoxib, 6-methoxy-2-naphtyl acetic acids, diclofenac, etodolac, ketoprofen, ketorolac, meloxicam, acetaminophen, or other, to treat the inflammation and pain within and around the disc 100.

The peri-shunt injectable 446 can be an inhibitor of nitric oxide synthase, such as methylene blue, 3-[(R)-2-carboxypiperazin-4-yl]-prop-2-enyl-1-phosphonic acid, 3-[(S)-2-carboxypiperazin-4-yl]-prop-2-enyl-1-phosphonic acid, tramadol, methadone, N(G)-nitro-L-arginine, N(G)-nitro-D-arginine, N(G)-methyl-L-arginine, N(G)-nitro-L-arginine methyl ester, 7-nitroindazole, N-iminoethyl-L-lysine, dimethyl arginine, N-[3-(aminomethyl)benzyl]acetamidine, miconazole, N-methylsulfonyl-6-(2-propargyloxyphenyl) hexanamide, aminoguanidine, lipochroman-6,methylprednisolone, indomethacin, or other, to treat the inflammation within and around the disc 100.

The peri-shunt injectable 446 can be an inhibitor of N-methyl-D-aspartate receptor (NMDA), such as ketamine, magnesium sulfate, magnesium chloride, magnesium hydroxide, amantadine, dextromethorphan, dextrorphan, ibogaine, phencyclidine, riluzole, tiletamine, dizocilpine (MK-801), aptiganel, memantine, remacimide, 7-chlorokynurenate, 5-, 7-dichlorokynurenic, kynurenic acid, 2-amino-7-phosphonoheptanoic acid, R-2-amino-5-phosphonopentanoate, 3-[(R)-2-carboxypiperazin-4-yl]-prop-2-enyl-1-phosphonic acid, or other, to minimize pain.

The peri-shunt injectable 446 can be an inhibitor of tumor necrosis factor alpha, such as thalidomide, doxycycline, naproxen, or other, to treat the inflammation within and around the disc 100.

The peri-shunt injectable 446 can be an inhibitor of 5-lipoxygenase, such as naproxen, or other, to treat the inflammation within and around the disc 100.

The peri-shunt injectable 446 can be a non-steroidal anti-inflammatory drug, such as naproxen, flurbiprofen, diclofenac with misoprostal, celecoxib, sulindac, oxaprozin, piroxicam, meloxicam, ketoprofen, nabumetone, ketorolac, robecoxib, or other, to treat inflammatory pain.

The peri-shunt injectable 446 can be a steroidal anti-inflammatory drug, such as dexamethasone, prednisone, methylprednisolone, or other, to treat inflammatory pain.

The peri-shunt injectable 446 can be an antibiotic, such as doxycycline, tetracycline, cephalosporin, penicillin, or other, to treat the bacterial infection within and around the disc 100.

The peri-shunt injectable 446 can be a muscle relaxant, such as cyclobenzaprine, orphenadrine, methocarbamol, diazepam, alprazolam, tizanidine, or other, to minimize stiffness and muscle pain.

The peri-shunt injectable 446 can be an anticonvulsant, such as aldehyde, aromatic allylic alcohol, barbiturate, benzodiazepine, bromide, carbamate, carboxamide, fatty acid, fructose derivative, gaba analog, hydantoin, oxazolidinedione, propionate, pyrimidinedione, pyrrolidine, succinimide, sulfonamide, triazine, urea, valproylamide, or other, to calm or stabilize the nerves and minimize the pain.

The anticonvulsant peri-shunt injectable 446 can be one of the approved anticonvulsant drugs, such as acetazolamide, carbamazepine, clobazam, clonazepam, diazepam, divalproex sodium, ethosuximide, ethotoin, felbamate, fosphenytoin, gabapentin, lamotrigine, levetiracetam, mephenytoin, metharbital, methsuximide, methazolamide, mexiletine, oxcarbazepine, phenobarbital, phenytoin, phensuximide, pregabalin, primidone, sodium valproate, stiripentol, tiagabine, topiramate, trimethadione, valproic acid, vigabatrin, zonisamide, or other, to reduce excitability of the nerve for reducing pain.

The peri-shunt injectable 446 can be an antidepressant, such as tricyclic antidepressant, amitriptyline, desipramine, duloxetine, nortriptyline, doxepin, or other, to sedate the sensation of pain or erase/reduce the neuronal memory of pain.

The peri-shunt injectable 446 can be a buffer or alkaline agent, such as sodium carbonate, sodium bicarbonate, potassium carbonate, potassium bicarbonate, magnesium carbonate, calcium carbonate, barium carbonate, potassium phosphate, sodium phosphate, magnesium oxide, magnesium hydroxide, sodium hydroxide, potassium hydroxide, barium hydroxide, cesium hydroxide, strontium hydroxide, calcium hydroxide, lithium hydroxide, rubidium hydroxide, neutral amines, or other, to neutralize lactic acid within the avascular disc 100 and surrounding tissue for alleviating pain caused by acid irritation.

The peri-shunt injectable 446 can be a calcium channel blocker, such as ziconotide, amlodipine, aranidipine, azelnidipine, barnidipine, benidipine, cilnidipine, clevidipine, efonidipine, felodipine, isradipine, lacidipine, magnesium ion, manidipine, lercanidipine, nicardipine, nifedipine, nilvadipine, nimodipine, nisoldipine, nitrendipine, pranidipine, gallopamil, verapamil, diltiazem, or other, to reduce pain.

The peri-shunt injectable 446 can be a nerve toxin, such as botulinum toxin (BOTOX®), Isopropyl methylphosphonofluoridate (Sarin), Pinacolyl Methylphosphonofluoridate (Soman), O-ethyl dimethylamidophosphorylcyanide (Tabun), S-[2-(diisopropylamino)ethyl]-O-ethyl methylphosphonothioate), saporin (SAP), or other, to intoxicate or destroy the nerve responsible for pain signal transmission.

The peri-shunt injectable 446 can be a nutrient, such as sulfate, amino acid, glucose, glucuronic acid, galactose, galactosamine, glucosamine, hydroxylysine, hydroxyproline, serine, threonine, boron, boric acid, magnesium trisilicate, magnesium mesotrisilicate, magnesium oxide, magnesium chloride, magnosil, pentimin, trisomin, orthosilicic acid, magnesium trisilicate pentahydrate, serpentine, sodium metasilicate, silanolates, silanol group, sialic acid, silicic acid, or other, to nourish or regenerate the degenerated disc 100.

The peri-shunt injectable 446 can be a growth factor, such as OP-1, TGF-beta, or other to promote disc 100 regeneration and increase disc height for reducing pain from facet loading and/or spinal stenosis.

The peri-shunt injectable 446 can be an inhibitor of fibrous encapsulation over the shunts 126, 373, such as azathioprine, 5-fluorouracil, mitomycin-C, halofuginone, anakinra, isoxazoles, leflunomide, mycophenolate, thalidomide, cyclosporine, abetimus, gusperimus, dexamethasone, prednisolone, methylprednisolone, steroid, or other, to delay, minimize or prevent fibrotic encapsulation over the shunts 126, 373.

The peri-shunt injectable 446 can be an anti-angiogenic compound, such as marimastat, Bay 12-9566, AG3340, CGS 27023A, COL-3, Tetracycline®, Neovastat, Sainte-Foy, BMS-275291, TNP-470, thalidomide, squalamine, Combretastatin A-4, endostatin collagen XVIII fragment, anti-VEGF Antibody, SU5416, SU6668, PTK787/ZK 22584, interferon-alpha, EMD121974, CAI, interleukin-12, IM862, Avastin, Celebrex, Erbitux, Herceptin, Iressa, Taxol, Velcade, TNP-470, CM101, carboxyamido-triazole, anti-neoplastic urinary protein, isotretionin, tamoxifen, tecogalan combrestatin, cyclophosphamide, angiostatin, platelet factor-4, Anginex, eponemycin, epoxomicin, epoxy-β-aminoketone, antiangiogenic antithrombin III, canstatin, cartilage-derived inhibitor, CD59 complement fragment, fibronectin fragment, gro-beta, heparinases, heparin hexasaccharide fragment, human chorinonic gonadotropin, interferon beta, interferon gamma, interferon inducible protein (IP-10), interleukin-12 (IL-12), Kringle 5 (plasminogen fragment), tissue inhibitors of metalloproteinases, 2-methoxyestradiol (Panzem), placental ribonuclease inhibitor, plasminogen activator inhibitor, prolactin 16 kD fragment, retinoids, tetrahydrocortisol-S, thrombospondin-1, transforming growth factor beta, vasculostatin, vasostatin (calreticulin fragment), or other, to minimize, delay or prevent ingrowth of blood vessels or nerves into the disc 100.

The peri-shunt injectable 446 can be a chemotherapy drug to treat tumor in the spine.

In addition, the disc shunt 126 and/or the linked shunt 373 can be coated or loaded with one or more of the peri-shunt injectables 446, before being inserted into the introducer needle 230. The peri-shunt injectables 446 can be loaded and dried on the matrix of the disc shunts 126, 373 to increase concentration and effectiveness of the injectable 446.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments.

It should be clear to one skilled in the art that the current chemicals, biochemicals, drugs, methods, embodiments, materials, constructions, cells, tissues or sites are not the only uses for which the invention may be used. Different constructions, methods, or designs for the introducer needle 230, trocar 441 or shunt-delivery needle 101 can be substituted and used. Different chemicals, minerals, drugs and growth factors can also be used as the peri-shunt injectable 446. Nothing in the preceding description should be taken to limit the scope of the present invention. The full scope of the invention is to be determined by the appended claims.

What is claimed is:

1. A disc shunt delivery device for treating a degenerated intervertebral disc, the delivery device comprising:
    a first shaft having a first lumen extending from proximal to distal end, said first shaft further comprising a pointed distal tip,
    a second shaft having a second lumen extending from proximal to distal end,
    wherein a distal portion of said first shaft is extended beyond a distal end of said second shaft, and
    a longitudinal slit formed by overlapping a longitudinal edge of said first lumen and with a longitudinal edge of said second lumen, said longitudinal slit thereby connecting said first and second lumens,
    wherein said first shaft, second shaft and longitudinal slit comprises a first position and a second position,
    wherein in said first position, said first shaft, second shaft and longitudinal slit further comprise a trocar,
    wherein said trocar comprises a cross-section shaped to fit within said first lumen, second lumen and longitudinal slit entirely,
    and wherein in said second position, said trocar is withdrawn from said first lumen, second lumen and longitudinal slit.

2. A disc shunt delivery device of claim 1, wherein in said second position, said first lumen houses a first proximal end of a U-shaped disc shunt,
    wherein said second lumen houses a second proximal end of said U-shaped disc shunt, and
    wherein said distal portion of said U-shaped disc shunt passes through said longitudinal slit.

3. A disc shunt delivery device of claim 1, further comprising a peri-shunt injection needle loaded with a drug into at least one of said first lumen and second lumen.

4. The disc shunt delivery device of claim 3, wherein said drug is an analgesic.

5. The disc shunt delivery device of claim 4, wherein said analgesic is chosen from the group consisting of bupivacaine, lidocain, ketorolac and Sarapin®.

6. The disc shunt delivery device of claim 3, wherein said drug is an opioid or narcotic.

7. The disc shunt delivery device of claim 6, wherein said drug is chosen from the group consisting of fentanyl, methadone, morphine, oxycodone, propoxyphene, meperidine, hydromorphone, codeine and hydrocodone.

8. The disc shunt delivery device of claim 3, wherein said drug is an inhibitor of cyclooxygenases.

9. The disc shunt delivery device of claim 8, wherein said drug is chosen from the group consisting of aspirin (acetylsalicylic acid or 2-acetoxybenzoic acid), ibuprofen (iso-butyl-propanoic-phenolic acid), naproxen [(+)-(S)-2-(6-methoxynaphthalen-2-yl) propanoic acid], celecoxib {4-[5-(4-methylphenyl)-3-(trifluoromethyl)pyrazol-1-yl] benzenesulfonamide}, rofecoxib, 6-methoxy-2-naphtyl acetic acids, diclofenac, etodolac, ketoprofen, ketorolac, meloxicam and acetaminophen.

10. The disc shunt delivery device of claim 3, wherein said drug is an inhibitor of nitric oxide synthase.

11. The disc shunt delivery device of claim 10, wherein said drug is chosen from the group consisting of methylene blue, 3-[(R)-2-carboxypiperazin-4-yl]-prop-2-enyl-1-phosphonic acid, 3-[(S)-2-carboxypiperazin-4-yl]-prop-2-enyl-1-phosphonic acid, tramadol, methadone, N(G)-nitro-L-arginine, N(G)-nitro-D-arginine, N(G)-methyl-L-arginine, N(G)-nitro-L-arginine methyl ester, 7-nitroindazole, N-iminoethyl-L-lysine, dimethyl arginine, N-[3-(aminomethyl)benzyl] acetamidine, miconazole, N-methylsulfonyl-6-(2-propargyloxyphenyl)hexanamide, aminoguanidine, lipochroman-6, methylprednisolone and indomethacin.

12. The disc shunt delivery device of claim 3, wherein said drug is an inhibitor of N-methyl-D-aspartate receptor (NMDA).

13. The disc shunt delivery device of claim 12, wherein said drug is chosen from the group consisting of ketamine, magnesium sulfate, magnesium chloride, magnesium hydroxide, amantadine, dextromethorphan, dextrorphan, ibogaine, phencyclidine, riluzole, tiletamine, dizocilpine (MK-801), aptiganel, memantine, remacimide, 7-chlorokynurenate, 5-, 7-dichlorokynurenic, kynurenic acid, 2-amino-7-phosphonoheptanoic acid, R-2-amino-5-phosphonopentanoate and 3-[(R)-2-carboxypiperazin-4-yl]-prop-2-enyl-1-phosphonic acid.

14. The disc shunt delivery device of claim 3, wherein said drug is an inhibitor of tumor necrosis factor alpha.

15. The disc shunt delivery device of claim 14, wherein said drug is chosen from the group consisting of thalidomide, doxycycline and naproxen.

16. The disc shunt delivery device of claim 3, wherein said drug is an inhibitor of 5-lipoxygenase.

17. The disc shunt delivery device of claim 3, wherein said drug is a non-steroidal anti-inflammatory drug.

18. The disc shunt delivery device of claim 17, wherein said drug is chosen from the group consisting of naproxen, flurbiprofen, diclofenac with misoprostal, celecoxib, sulindac, oxaprozin, piroxicam, meloxicam, ketoprofen, nabumetone, ketorolac and robecoxib.

19. The disc shunt delivery device of claim 3, wherein said drug is a steroidal anti-inflammatory drug.

20. The disc shunt delivery device of claim 19, wherein said drug is chosen from the group consisting of dexamethasone, prednisone and methylprednisolone.

21. The disc shunt delivery device of claim 3, wherein said drug is an antibiotic.

22. The disc shunt delivery device of claim 21, wherein said drug is chosen from the group consisting of doxycycline, tetracycline, cephalosporin and penicillin.

23. The disc shunt delivery device of claim 3, wherein said drug is a muscle relaxant.

24. The disc shunt delivery device of claim 23, wherein said drug is chosen from the group consisting of cyclobenzaprine, orphenadrine, methocarbamol, diazepam, alprazolam and tizanidine.

25. The disc shunt delivery device of claim 3, wherein said drug is an anticonvulsant.

26. The disc shunt delivery device of claim 25, wherein said drug is chosen from the group consisting of aldehyde, aromatic allylic alcohol, barbiturate, benzodiazepine, bromide, carbamate, carboxamide, fatty acid, fructose derivative, gaba analog, hydantoin, oxazolidinedione, propionate, pyrimidinedione, pyrrolidine, succinimide, sulfonamide, triazine, urea, valproylamide, acetazolamide, carbamazepine, clobazam, clonazepam, diazepam, divalproex sodium, ethosuximide, ethotoin, felbamate, fosphenyloin, gabapentin, lamotrigine, levetiracetam, mephenyloin, metharbital, methsuximide, methazolamide, mexiletine, oxcarbazepine, phenobarbital, phenyloin, phensuximide, pregabalin, primidone, sodium valproate, stiripentol, tiagabine, topiramate, trimethadione, valproic acid, vigabatrin and zonisamide.

27. The disc shunt delivery device of claim 3, wherein said drug is an antidepressant.

28. The disc shunt delivery device of claim 27, wherein said drug is chosen from the group consisting of tricyclic antidepressant, amitriptyline, desipramine, duloxetine, nortriptyline and doxepin.

29. The disc shunt delivery device of claim 3, wherein said drug is a buffer or alkaline agent.

30. The disc shunt delivery device of claim 29, wherein said drug is chosen from the group consisting of sodium carbonate, sodium bicarbonate, potassium carbonate, potassium bicarbonate, magnesium carbonate, calcium carbonate, barium carbonate, potassium phosphate, sodium phosphate, magnesium oxide, magnesium hydroxide, sodium hydroxide, potassium hydroxide, barium hydroxide, cesium hydroxide, strontium hydroxide, calcium hydroxide, lithium hydroxide, rubidium hydroxide and neutral amines.

31. The disc shunt delivery device of claim 3, wherein said drug is a calcium channel blocker.

32. The disc shunt delivery device of claim 31, wherein said drug is chosen from the group consisting of ziconotide, amlodipine, aranidipine, azelnidipine, barnidipine, benidipine, cilnidipine, clevidipine, efonidipine, felodipine, isradipine, lacidipine, magnesium ion, manidipine, lercanidipine, nicardipine, nifedipine, nilvadipine, nimodipine, nisoldipine, nitrendipine, pranidipine, gallopamil, verapamil and diltiazem.

33. The disc shunt delivery device of claim 3, wherein said drug is a nerve toxin.

34. The disc shunt delivery device of claim 33, wherein said drug is chosen from the group consisting of botulinum toxin (BOTOX®), Isopropyl methylphosphonofluoridate (Sarin), Pinacolyl Methylphosphonofluoridate (Soman), O-ethyl dimethylamidophosphorylcyanide (Tabun), S[2-(diisopropylamino)ethyl]-O-ethyl methylphosphonothioate) and saporin (SAP).

35. The disc shunt delivery device of claim 3, wherein said drug is a nutrient.

36. The disc shunt delivery device of claim 35, wherein said drug is chosen from the group consisting of sulfate, amino acid, glucose, glucuronic acid, galactose, galactosamine, glucosamine, hydroxylysine, hydroxylproline, serine, threonine, boron, boric acid, magnesium trisilicate, magnesium mesotrisilicate, magnesium oxide, magnesium chloride, magnosil, pentimin, trisomin, orthosilicic acid, magnesium trisilicate pentahydrate, serpentine, sodium metasilicate, silanolates, silanol group, sialic acid and silicic acid.

37. The disc shunt delivery device of claim 3, wherein said drug is a growth factor.

38. The disc shunt delivery device of claim 37, wherein said drug is chosen from the group consisting of OP-1 and TGF-beta.

39. The disc shunt delivery device of claim 3, wherein said drug is an inhibitor of fibrous encapsulation over the disc shunts.

40. The disc shunt delivery device of claim 39, wherein said drug is chosen from the group consisting of azathioprine, 5-fluorouracil, mitomycin-C, halofuginone, anakinra, isoxazoles, leflunomide, mycophenolate, thalidomide, cyclosporine, abetimus, gusperimus, dexamethasone, prednisolone, methylprednisolone and steroid.

41. The disc shunt delivery device of claim 3, wherein said drug is an anti-angiogenic compound.

42. The disc shunt delivery device of claim 41, wherein said drug is chosen from the group consisting of marimastat, Bay 12-9566, AG3340, CGS 27023A, COL-3, Tetracycline®, Neovastat, Sainte-Foy, BMS-275291, TNP-470, thalidomide, squalamine, Combretastatin A-4, endostatin collagen XVIII fragment, anti-VEGF Antibody, SU5416, SU6668, PTK787/ZK 22584, interferon-alpha, EMD121974, CAI, interleukin-12, IM862, Avastin, Celebrex, Erbitux, Herceptin, Iressa, Taxol, Velcade, TNP-470, CM101, carboxyamido-triazole, anti-neoplastic urinary protein, isotretinin, tamoxifen, tecogalan combrestatin, cyclophosphamide, angiostatin, platelet factor-4, Anginex, eponemycin, epoxomicin, epoxy-β-aminoketone, antiangiogenic antithrombin III, canstatin, cartilage-derived inhibitor, CD59 complement fragment, fibronectin fragment, gro-beta, heparinases, heparin hexasaccharide fragment, human chorinonic gonadotropin, interferon beta, interferon gamma, interferon inducible protein (IP-10), interleukin-12 (IL-12), Kringle 5 (plasminogen fragment), tissue inhibitors of metalloproteinases, 2-methoxyestradiol (Panzem), placental ribonuclease inhibitor, plasminogen activator inhibitor, prolactin 16 kD fragment, retinoids, tetrahydrocortisol-S, thrombospondin-1, transforming growth factor beta, vasculostatin and vasostatin (calreticulin fragment).

43. The disc shunt delivery device of claim 3, wherein said drug is a chemotherapy drug.

* * * * *